US00PP14256P29

(12) United States Plant Patent
Hanes

(10) Patent No.: US PP14,256 P2
(45) Date of Patent: Oct. 28, 2003

(54) PETUNIA PLANT NAMED 'WHIP ABLOS'

(50) Latin Name: *Petunia hybrida*
Varietal Denomination: 'Whip Ablos'

(75) Inventor: Mitchell Eugene Hanes, Morgan Hill, CA (US)

(73) Assignee: Goldsmith Seeds Inc., Gilroy, CA (US)

( * ) Notice: Subject to any disclaimer, the term of this patent is extended or adjusted under 35 U.S.C. 154(b) by 0 days.

(21) Appl. No.: 10/382,421

(22) Filed: Mar. 5, 2003

(51) Int. Cl.[7] ..... A01H 5/00
(52) U.S. Cl. ..... Plt./356
(58) Field of Search ..... Plt./356

*Primary Examiner*—Kent Bell
(74) *Attorney, Agent, or Firm*—Jondle & Associates P.C.

(57) ABSTRACT

A petunia cultivar particularly distinguished by light pink colored flowers with a hint of red-purple, compact habit and good basal branching.

1 Drawing Sheet

Genus and species: *Petunia hybrida.*
Variety denomination: 'Whip Ablos'.

BACKGROUND OF THE NEW PLANT

The present invention comprises a new and distinct cultivar of petunia, botanically known as *Petunia hybrida,* and hereinafter referred to by the cultivar name 'Whip Ablos'. The new cultivar is asexually reproduced from vegetative cuttings and tissue culture resulting from the cross of the seed/pod parent 00-382-1, a single pink proprietary line that is unnamed and unpatented×00-341-1, a single dull pink proprietary line that is unnamed and unpatented.

'Whip Ablos' is a product of a planned breeding program intended to create new petunia plants with light pink colored flowers with a hint of red-purple, compact habit, good basal branching and moderately vigorous growth.

The new cultivar was created in 2000 in Gilroy, Calif. and has been asexually reproduced repeatedly by vegetative cuttings and tissue culture in Gilroy, Calif., Andijk, The Netherlands, and Guatemala over a two and half year period. The plant has also been trialed at Gilroy, Calif., Litchfield, Mich. and Andijk, The Netherlands. The present invention has been found to retain its distinctive characteristics through successive asexual propagations; and this novelty is firmly fixed.

DESCRIPTION OF PHOTOGRAPH

This new petunia plant is illustrated by the accompanying photograph which shows blooms and foliage of the plant in full color, the colors shown being as true as can be reasonably obtained by conventional photographic procedures.

DESCRIPTION OF THE NEW CULTIVAR

The following detailed descriptions set forth the distinctive characteristics of 'Whip Ablos'. The data, which defines these characteristics, were collected from asexual reproductions carried out in Gilroy, Calif. The plant history was taken on 10 months old plants grown in one-gallon pots in fall/winter season, in a poly-covered greenhouse under 2–4 hours supplemental light and color readings were taken in the greenhouse in the winter season under natural light. Plants had been cut back numerous times prior to data readings being taken. Color references are primarily to The R.H.S. Colour Chart of The Royal Horticultural Society of London (R.H.S.). Texture description details were observed under a dissecting microscope according to The New Royal Horticultural Society Dictionary of Gardening (1992).

THE PLANT

Classification:
*Botanical.*—Petunia hybrida.
*Commercial.*—Petunia.
Form: Semi upright and decumbent.
Growth and branching habit: Good vigorous habit, well-branched, full plant.
Height: From soil level to top of blooms: Approximately 20–25 cm.
Width: Approximately 40–50 cm including flowers.
Time to produce a finished flowering plant: 9–11 weeks.
Outdoor plant performance: Full sun, free- flowering through the summer, some heat tolerance. Use in hanging baskets, mixed containers, window boxes and mass plantings.
Time to initiate roots: Approximately 18–23 days in the greenhouse.
Root description: Fibrous, white.

THE LEAVES

Arrangement: Alternate, upper leaves sub-opposite.
Length: 4.5–5.3 cm.
Width: 2.3–3.5 cm.
Leaf blade shape: Ovate.
Leaf margin: Entire.
Apex aspect: Acute.
Base aspect: Acuminate.
Leaf color: Upper side; RHS 137A (green); Underside; RHS 138A/B (green).
Texture: Short glandular hairs.
Venation: Palmate.
Venation color: RHS 144B (yellow-green).
Petiole length: 0.2–0.3 cm.
Petiole width: 0.2 cm.
Petiole color: RHS 144B (yellow-green).
Petiole texture: Glandular hairs of various sizes.

THE STEM

Length: 30–40 cm.
Diameter: 2.5–3.5 cm.
Internode length: 1.0–4.0 cm.
Color: RHS 144A (yellow-green).
Texture: Glandular hair of various sizes.
Stem anthocyanin: None.
Peduncle color: RHS 144A (yellow-green).
Peduncle length: 3.5–4.5 cm.
Peduncle diameter: 1.0 cm.
Peduncle texture: Glandular hairs of various sizes.

THE BUD

Shape: Oblong.
Diameter: 0.4–0.5 cm.
Length: 1.3–2.7 cm.
Color at tight bud: RHS 149D (yellow-green) and RHS 150D (yellow-green) with RHS 152A (yellow-green) mid-veins.

THE FLOWER

Blooming habit: Continuous all through the growing season. Good floriferousness.
Inflorescence type: Flowers in upper leaf axis.
Young flower color: Color ranges from base of RHS 76D (purple), with a margin and blush of RHS N74D (red-purple); veining RHS 73A (red-purple); to heavy base color of RHS 74D (red-purple), with a margin of RHS 74C (red-purple)
Young flower floret diameter: 2.9–3.3 cm.
Mature flower color: Front side, base color RHS 76D (purple) but more white, with a hint of RHS N74D (red-purple) as a blush at margins and corolla, veining from corolla into petals of subdued hue of RHS N77B (purple), and RHS 73B (red-purple), mid-veins of RHS 70C (red-purple) overlaid with a slight greenish hue of very subdued RHS 151A (yellow-green). All colors fade irregularly with maturity. Underside, base color RHS 76D (purple) but little more white, margins of a hint RHS 74C (red-purple), mid-veins RHS 144B (yellow-green).
Corolla tube color inside: Base color RHS 76D (purple), mid-veins RHS 70C (red-purple) overlaid with a slight greenish hue of very subdued RHS 151A (yellow-green), secondary veining of RHS N77B (purple).
Corolla tube length: 2.2–2.5 cm.
Corolla outside texture: Glandular hairs of various sizes.
Floret form and number of petals: Funnel form, 5 lobed petals (single type) fused at base.
Flower (limb) diameter: 3.5–3.9 cm.
Petal apex shape: Acute, some petals slight praemorse.
Petal margin: Entire.
Petal waviness (ruffle of petal): Weak.
Petal lobation: Moderate.
Petal texture: Papillose.
Caylx: 5 deeply lobed sepals, fused at base.
Sepal color: RHS 138A (green).
Sepal length: 1.8–2.2 cm.
Sepal width: 0.3–0.4 cm.
Sepal shape: Oblong.
Sepal apex: Acute.
Sepal texture: Glandular hairs of various sizes.
Lastingness of individual blooms: 4–8 days.
Fragrance: None.

THE REPRODUCTIVE ORGANS

Stamens: Five, 2 taller and 3 shorter.
Filament color: RHS 155C (white).
Pollen color: RHS 2D (yellow).
Pistil: One.
Stigma: RHS 144A (yellow-green) and outer portion of RHS 145B (yellow-green).
Style color: RHS 145B (yellow-green).
Fruit seed set: Not observed.

DISEASE AND INSECT RESISTANCE

Not observed.

COMPARISON WITH KNOWN CULTIVARS

Compared to the female parent 00-382-1 in the following ways: The female parent has a small pink flower while the 'Whip Albos' has a small light pink (appleblossom) color. The female parent is less vigorous than the 'Whip Ablos'.

Compared to the male parent. 00-341-1 in the following ways: The male parent has a dull solid pink color while the 'Whip Ablos' has a very light pink (appleblossom) color. The male parent is later to flower than the 'Whip Ablos', and produces fewer flowers on the plant than does 'Whip Ablos'.

I claim:

1. A new and distinct petunia plant as shown and described herein.

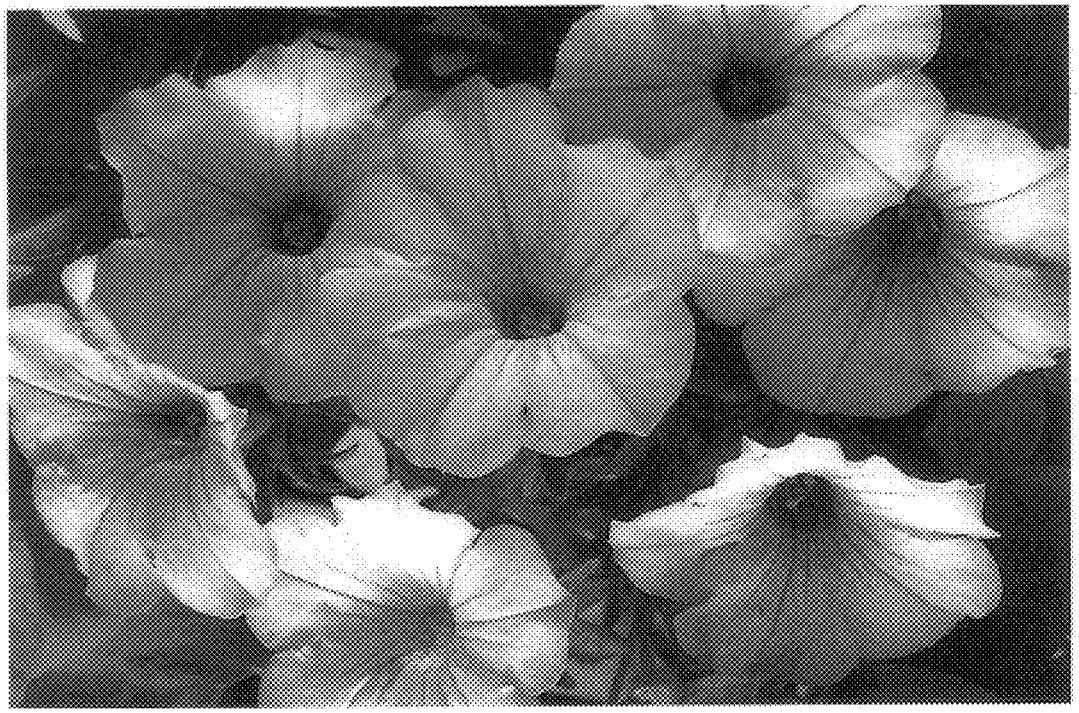

* * * * *